(12) United States Patent
Cairo et al.

(10) Patent No.: US 9,399,653 B2
(45) Date of Patent: Jul. 26, 2016

(54) METHODS AND SYSTEMS FOR PREPARING IRREVERSIBLE INHIBITORS OF PROTEIN TYROSINE PHOSPHATASES

(75) Inventors: Christopher Warren Cairo, Edmonton (CA); Naresh Singh Tulsi, Dalkeith (AU); Alan Michael Downey, Edmonton (CA)

(73) Assignee: The Governors of the University of Alberta, Edmonton AB (CA)

( * ) Notice: Subject to any disclaimer, the term of this patent is extended or adjusted under 35 U.S.C. 154(b) by 263 days.

(21) Appl. No.: 13/582,407

(22) PCT Filed: Mar. 3, 2011

(86) PCT No.: PCT/CA2011/050126
§ 371 (c)(1),
(2), (4) Date: Mar. 12, 2013

(87) PCT Pub. No.: WO2011/106898
PCT Pub. Date: Sep. 9, 2011

(65) Prior Publication Data
US 2013/0165333 A1 Jun. 27, 2013

Related U.S. Application Data

(60) Provisional application No. 61/310,082, filed on Mar. 3, 2010.

(51) Int. Cl.
| | | |
|---|---|---|
| *A01N 43/00* | (2006.01) | |
| *A61K 31/33* | (2006.01) | |
| *C40B 30/04* | (2006.01) | |
| *C07D 303/02* | (2006.01) | |
| *C07D 303/36* | (2006.01) | |
| *C07F 9/38* | (2006.01) | |
| *C07K 5/08* | (2006.01) | |
| *C12Q 1/42* | (2006.01) | |
| *C07F 9/40* | (2006.01) | |
| *A61K 38/00* | (2006.01) | |

(52) U.S. Cl.
CPC ............ *C07F 9/3882* (2013.01); *C07F 9/4056* (2013.01); *C07K 5/0827* (2013.01); *C12Q 1/42* (2013.01); *A61K 38/00* (2013.01)

(58) Field of Classification Search
None
See application file for complete search history.

(56) References Cited

U.S. PATENT DOCUMENTS

| 5,395,827 A * | 3/1995 | Rzeszotarski et al. ........ 514/114 |
| 7,504,389 B2 | 3/2009 | Blaskovich et al. |
| 8,445,706 B2 | 5/2013 | Shen |
| 2010/0061936 A1 | 3/2010 | Shen |

FOREIGN PATENT DOCUMENTS

CA 2586363 5/2006

OTHER PUBLICATIONS

STN CAS RN: 170516-01-5 (entered STN Nov. 22, 1995).*
CAS RN 1213253-26-9 (identified in IDS of Jul. 2, 2015).*
A. M. Downey, C.W. Cairo (Sep. 2014) "Synthesis of a-brominated phosphonates and their application as phosphate bioisosteres," Med. Cem. Commun. 5, 1619 (Royal Society of Chemistry).
Burke, T. et al. (1996) Small Molecule Interactions with Protein-Tyrosine Phosphatase PTPIB and Their Use in Inhibitor Drugs, Biochemistry 35:15989-15996.
Kole, H. et al. (1995) Phosphonate Inhibitors of protein-tyrosine and serine/threonine phosphatases, Biochem. J. 311:1025-1031.
Burke,Jr, TR et al. (1993) Preparation of Fluoro- and Hydroxy-4-(phosphonomethyl)-D,L-phenylalanine Suitably Protected for Solid-Phase synthesis of Peptides Containing Hydrolytically Stable Analogues of O-Phosphotyrosine J. Org. Chern. 1993, 58, 1336-1340.
Burke Jr, TR, and Zhang, ZY (1998) Protein-tyrosine phosphatases: Structure, mechanism, and inhibitor discovery, Biopolymers 47, 225-241.
Chen, L et al. (1995) Why is Phosphonodifluoromethyl Phenylalanine a More Potent Inhibitory Moiety Than Phosphonomethyl Phenylalanine toward Protein-Tyrosine Phosphatases? Biochemical and Biophysical Research Communications 1995, 216(3), 976-984.
Green, D et al.(1996) The Facile Synthesis of 0,0-Dialkyl alpha-halobenzylphosphonates from O,O-Dialkyl alpha-hydroxybenzylphosphonates Tetrahedron 52(30), 10215-10224.
Hubbard, CE, and Barrios, AM (2008) A highly efficient route to enantiomerically pure I-N-Bz-Pmp(t-Bu)2-OH and incorporation into a peptide-based protein tyrosine phosphatase inhibitor, Bioorg. Med. Chem. Lett. 18, 679-681.
Kumar, S et al. (2004) Activity-based probes for protein tyrosine phosphatases Proc. Natl. Acad. Sci. U.S.A. 101(21), 7943-7948.
Lee, K., Gao, Y., Yao, Z. J., Phan, J., Wu, L., Liang, J., Waugh, DS, Zhang, ZY, and Burke Jr, TR. (2003) Tripeptide inhibitors of Yersinia protein-tyrosine phosphatase, Bioorg. Med. Chem. Lett. 13, 2577-2581.
Leung, C., Grzyb, J., Lee, J., Meyer, N., Hum, G., Jia, C., Liu, S., and Taylor, SD (2002) The difluoromethylenesulfonic acid group as a monoanionic phosphate surrogate for obtaining PTP1B inhibitors, Bioorg. Med. Chem. 10, 2309-2323.

(Continued)

*Primary Examiner* — Jared D Barksy
(74) *Attorney, Agent, or Firm* — Lathrop & Gage LLP

(57) ABSTRACT

Described herein are the preparation and use of novel bromophosphonomethylphenylalanine amino acid derivatives (BrPmp) and BrPmp-containing peptides as specific, irreversible protein tyrosine phosphatase inhibitors, which are suitable for application in peptide synthesis. These derivatives are particularly advantageous since their synthesis is both easy and scalable, and they are suitable for peptide synthesis. The BrPmp derivatives described herein can be appropriately protected to allow for solid phase peptide synthesis (SPPS) and incorporation into peptides for preparation of protein tyrosine phosphatase inhibitors and inhibitor libraries. The peptides and peptide libraries can be used to identify new protein tyrosine phosphatase specific sequences and profile protein tyrosine phosphatase activity in cell lysates, diagnostic samples and biopsy samples.

9 Claims, 13 Drawing Sheets

(56) References Cited

OTHER PUBLICATIONS

Li, P., Zhang, M., Peach, ML, Liu, H., Yang, D., and Roller, PP(2003) Concise and enantioselective synthesis of Fmoc-Pmp(But) 2-OH and design of potent Pmp-containing Grb2-SH2 domain antagonists, Org. Lett. 5, 3095-3098.

Qabar, MN., Urban, J., and Kahn, M. (1997) A facile solution and solid phase synthesis of phosphotyrosine mimetic L-4-[diethylphosphono(difluoromethyl)]-phenylalanine (F2Pmp(EtO)$_2$) derivatives, Tetrahedron 53, 11171-11178.

Taylor, WP et al. (1996) Quiescent Affinity Inactivators of Protein Tyrosine Phosphatases Bioorg. Med. Chem. 4(9), 1515-1520.

Tulsi, NS et al. (Sep. 2010) A protected L-bromophosphonomethylphenylalanine amino acid derivative 1-3, 24, 26-48 (BrPmp) for synthesis of irreversible protein tyrosine phosphatase inhibitors Bioorg. Med. Chem. 2010, 18, 8679-8686.

Yokomatsu, T., Yamagishi, T., Matsumoto, K., and Shibuya, S. (1996) Stereocontrolled synthesis of hydroxymethylene phosphonate analogues of phosphorylated tyrosine and their conversion to monofluoromethylene phosphonate analogues, Tetrahedron 52, 11725-11738.

Zhang, ZY (2001) Protein tyrosine phosphatases: Prospects for therapeutics, Curr. Opin. Chem. Biol. 5, 416-423.

International Search Report and Written Opinion Corresponding to International Application No. PCT/CA2011/050126, Mailed Jun. 3, 2011.

International Preliminary Report of Patentability, Corresponding to International Application No. PCT/CA2008/000119, Issued Sep. 4, 2012.

Abstract, CAS Registry No. 1213253-26-9, SciFinder.

\* cited by examiner

METHODS AND SYSTEMS FOR PREPARING IRREVERSIBLE INHIBITORS OF PROTEIN TYROSINE PHOSPHATASES

CROSS-REFERENCE TO RELATED APPLICATION

This application claims priority to and the benefit of U.S. Provisional Patent Application No. 61/310,082, filed Mar. 3, 2010, entitled "Methods and Systems for Preparing Irreversible Inhibitors of Protein Tyrosine Phosphatases", which is incorporated herein by reference in its entirety.

FIELD OF THE INVENTION

The present invention relates to the field of protein tyrosine phosphatases, and more specifically, to irreversible inhibitors of protein tyrosine phosphatases and methods for synthesizing these inhibitors.

BACKGROUND

Protein tyrosine phosphatases (PTPs) are important for the regulation of signaling pathways, acting as a biochemical counterbalance to kinases.(1, 2) This mechanism plays diverse roles in biological systems, including the regulation of T cell antigen recognition and activation.(3) As a result, PTPs are an important target for both medicinal chemistry and biochemical research.(4, 5) However, few general strategies have been elucidated for the determination of PTP specificity or inhibitor design.

A well-studied immune cell PTP is CD45. CD45 is a receptor-like PTP (RPTP), and the most prevalent membrane-associated PTP in T cells.(6) Misregulation of CD45 results in severe combined immunodeficiency (SCID), and the receptor is implicated in autoimmune disease. Currently, the primary strategies to examine CD45 activity rely on the use of phosphotyrosine-specific antibodies, previously validated synthetic inhibitors, or the synthesis of phosphopeptide substrates.(7) These strategies severely limit the type and amount of data that can be collected on PTP's since they either are not specific to a particular PTP, as in the case of phosphotyrosine-specific antibodies, or else they require the identification and validation of a new compound, as in the case of synthetic inhibitors. Specific phosphopeptides have been used to study PTP activity, however these compounds require a separate detection strategy, such as an enzyme-linked method.(8) These strategies all suffer from difficulties due to poor signal-to-noise ratios, making it difficult to distinguish positive hits or small changes to PTPs activity. None of these strategies allow for detection by covalent labeling of the active PTPs. Moreover, the study and detection of PTPs is limited because of the lack of known specific inhibitors for desired PTPs having high potency.

The design of specific PTP inhibitors remains a challenge, and new strategies that provide enhanced activity or reduce development time are of continuing interest.(4) Currently, reversible and irreversible inhibitors of PTPs are known.

Many different reversible inhibitors of PTPs have been reported. A classic strategy for designing reversible, competitive PTP inhibitors has exploited non-hydrolyzable phosphotyrosine (pTyr) mimics, such as phosphonomethylphenylalanine (Pmp).(9) It has been previously shown that modification of Pmp to phosphonodifluoromethylphenylalanine ($F_2$Pmp) improves the potency of these derivatives (FIG. 1).(10) Reported derivatives of Pmp include fluoro, difluoro, chloro, and dichloro derivatives.(10-14) These strategies have been successfully applied to develop many different competitive inhibitors for a variety of PTPs.(15) However, these types of PTP inhibitors have many different disadvantages. For example, reversible inhibitors often have low specificity for the target PTP, and can inhibit undesired targets. Many also have low potency (affinity), therefore reducing their utility in medicinal chemistry or biological applications. Reversible PTP inhibitors have limited use in the detection of PTPs in microscopy, histology, proteomic, or diagnostic tests and they cannot be used in enzyme labeling strategies. These disadvantages seriously hinder the study of PTPs in medicinal chemistry and biochemical research.

In recent years, there has been renewed interest in identifying irreversible or covalent inhibitors of a variety of enzymes, including PTPs. In addition to improved potency, irreversible inhibitors (sometimes referred to as suicide substrates) can be of interest in the development of enzyme labeling strategies. For example, irreversible inhibitors, when attached to fluorophores or affinity tags, have been employed as activity-based protein probes (ABPP).(16, 17) Known irreversible inhibitors of PTPs include quinone methides,(18) aryl vinyl sulfonates,(19) nitrostyrene,(20) and α-bromobenzylphosphonate (BBP) derivatives.(21, 22) Other notable strategies have included the synthesis of fluorogenic substrates of PTPs, which should allow improved assay, detection, and imaging applications.(23) Therefore, irreversible PTP inhibitors can provide a means to label and detect enzyme activity with great sensitivity.

Widlanski and coworkers first demonstrated that BBP derivatives could act as irreversible inhibitors of PTPs.(21) Kumar et al. subsequently tested the activity of α-bromobenzylphosphonate (BBP) analogs containing affinity tags to be used as a detection strategy for PTPs using biotin-labeled derivative 2 (FIG. 1).(22) These derivatives were found to form covalent adducts with PTPs, forming the basis of proteomic strategies for PTP identification. However, compound 2 was also shown to covalently label a wide variety of PTPs, establishing a major barrier to its use as a specific labeling agent for PTPs and limiting its application as an inhibitor of specific enzymes. Moreover, the synthesis of compound 2 is difficult, and not easily scalable. Due to its lack of specificity and difficulty in its synthetic preparation, compound 2 does not lend itself to identification of new and specific PTP inhibitors. For example, the compound could not be easily inserted into peptides via peptide synthesis techniques such as solid-phase peptide synthesis (SPPS). It can therefore not be used in the preparation of peptide libraries that can be used to find inhibitors for various PTPs.

Consequently, there is a need for methods and systems which can provide for the synthesis and identification new irreversible inhibitors of PTPs, which are both specific and potent, while avoiding some of the problems listed above. Such methods and systems could be used to expand our knowledge of PTPs, and allow for new methods to detect PTP activity and identify new PTP-specific substrate sequences.

SUMMARY

In accordance with a broad aspect of the invention, there is provided bromo-phosphonomethylphenylalanine amino acid derivatives of the Formula (I):

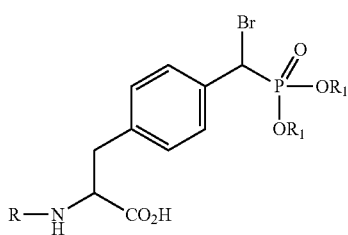

wherein R can be selected from the group consisting of Boc (butyloxycarbonyl), Fmoc (fluorenylmethyloxycarbonyl), Cbz (carboxybenzyl), H (hydrogen), and Alloc (allyloxycarbonyl); and wherein $R_1$ can be selected from the group consisting of methyl (—$CH_3$), ethyl (—$CH_2CH_3$), tert-butyl (—$C(CH_3)_3$), benzyl (—$CH_2C_6H_5$), allyl (—$CH_2CH$=$CH_2$), H (hydrogen), dimethylamino (—$N(CH_3)_2$), propylamino (—$NHCH_2CH_2CH_3$), isopropylamino (—$NHCH(CH_3)_2$), and acetate (—$C(O)CH_3$). In one aspect, R is hydrogen and $R_1$ is hydrogen. In one aspect, R is Fmoc and $R_1$ is methyl.

The bromo-phosphonomethylphenylalanine amino acid derivatives of the Formula (I) can be L-amino acid derivatives or D-amino acid derivatives. The α-bromo substituent may be a mixture of diastereomers or a single R or S diastereomer.

In one aspect, bromo-phosphonomethylphenylalanine amino acid derivatives of the Formula (I) can be used to inhibit protein tyrosine phosphatases. In one aspect, they can be used to inhibit CD45. In one aspect, they can be used for the detection of protein tyrosine phosphatases in tests selected from the group consisting of microscopy tests, histology tests, proteomic tests and diagnostic tests.

In accordance with another broad aspect of the invention, there is provided bromo-phosphonomethylphenylalanine amino acid derivatives of the Formula (II):

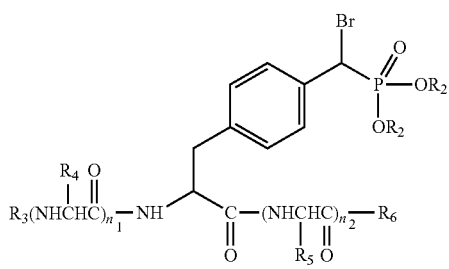

wherein $R_2$ can be selected from the group consisting of methyl (—$CH_3$), ethyl (—$CH_2CH_3$), tert-butyl (—$C(CH_3)_3$), benzyl (—$CH_2C_6H_5$), allyl (—$CH_2CH$=$CH$), H (hydrogen), dimethylamino (—$N(CH_3)_2$), propylamino (—$NHCH_2CH_2CH_3$), isopropylamino (—$NHCH(CH_3)_2$), and acetate (—$C(O)CH_3$); wherein $R_3$ can be selected from the group consisting of hydrogen, acetyl, alkanoyl, alkyl, aryl, aralkyl, alkaryl, and polyethyleneoxy; wherein $R_4$ and $R_5$ are side chains of amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, or derivatives thereof; wherein $R_6$ can be selected from the group consisting of hydroxyl, —$NH_2$, O-alkyl, O-aryl, O-alkaryl, and N-polyethyleneoxy; and wherein $n_1$ and $n_2$ may be the same or different, are zero, or 1-50, but wherein $n_1$ and $n_2$ are not zero at the same time, with the proviso that the substituents of Formula II which can be substituted are optionally substituted. In one aspect, $R_3$ is hydrogen, $R_4$ is the side chain of aspartic acid, $n_1$ is 1, $R_2$ is hydrogen, $R_5$ is the side chain of leucine, $R_6$ is hydroxyl, and $n_2$ is 1.

The amino acids and amino acid derivatives of the Formula (II) can be L-amino acids, L-amino acid derivatives, D-amino acids, or D-amino acid derivatives. The α-bromo substituent may be a mixture of diastereomers or a single R or S diastereomer.

In one aspect, bromo-phosphonomethylphenylalanine amino acid derivatives of the Formula (II) can be used to inhibit protein tyrosine phosphatases. In one aspect, they can be used to inhibit CD45.

In accordance with another broad aspect of the invention, the bromo-phosphonomethylphenylalanine amino acid derivatives of Formula (II) can be used to synthesize a library of peptide sequences. In one aspect, the library of peptide sequences can be used to prepare a multiplexed detection kit. In one aspect, the multiplexed detection kit can be used to profile protein tyrosine phosphatase activity in cell lysates, diagnostic samples and biopsy samples. In one aspect, the library of peptide sequences can be used to identify new protein tyrosine phosphatase specific sequences. In accordance with another broad aspect of the invention, there is provided a method of detecting a protein tyrosine phosphatase comprising the steps of introducing a bromo-phosphonomethylphenylalanine amino acid derivative of Formula (I) or Formula (II) to a sample during a microscopic test, histological test, proteomic test or diagnostic test.

In accordance with another broad aspect of the invention, there is provided a method of synthesizing a library of peptide sequences comprising the steps of preparing peptide sequences, wherein each peptide sequence comprises a bromo-phosphonomethylphenylalanine amino acid derivative of Formula (I) or Formula (II) and combining the peptide sequences to form the library.

In accordance with another broad aspect of the invention, there is provided a library of peptide sequences wherein each peptide sequence comprises a bromo-phosphonomethylphenylalanine amino acid derivative of Formula (I) or Formula (II).

In accordance with another broad aspect of the invention, there is provided a method of preparing a multiplexed detection kit to identify substrates and inhibitors of protein tyrosine phosphatases comprising the steps of preparing the library of peptide sequences wherein each peptide sequence contains a derivative of Formula (I) or Formulat (II), and introducing the library into the kit.

In accordance with another broad aspect of the invention, there is provided a multiplexed detection kit comprising the library of peptide sequences wherein each peptide sequence contains a derivative of Formula (I) or Formulat (II) to identify substrates and inhibitors of protein tyrosine phosphatases.

In accordance with another broad aspect of the invention, there is provided a method of profiling protein tyrosine phosphatase activity comprising the step of introducing a bromo-phosphonomethylphenylalanine amino acid derivative of Formula (I) or Formula (II) to cell lysates, diagnostic samples and biopsy samples.

In accordance with another broad aspect of the invention, there is provided a method of identifying new protein tyrosine phosphatase specific sequences comprising the steps of preparing bromo-phosphonomethylphenylalanine amino acid derivatives of Formula (I) or Formula (II), combining the derivatives to form the library and adding the library to a sample of protein tyrosine phosphatases.

In accordance with another broad aspect of the invention, there is provided a method of treating a human subject suffering from a disease caused by misregulation of protein tyrosine phosphatases, which can be severe combined immunodeficiency. The method comprises the step of detecting protein tyrosine phosphatases by adding a bromo-phosphonomethylphenylalanine amino acid derivative of Formula (I) or Formula (II) to tests selected from the group consisting of microscopy tests, histology tests, proteomic tests and diagnostic tests. In another embodiment, the method comprises the step of using the multiplexed detection kit to profile protein tyrosine phosphatase activity in cell lysates, diagnostic samples and biopsy samples.

BRIEF DESCRIPTION OF THE DRAWINGS

The present invention, both as to its organization and manner of operation, may best be understood by reference to the following description, and the accompanying drawings of various embodiments wherein like numerals are used throughout the several views, and in which.

DETAILED DESCRIPTION OF THE INVENTION

Figure 1:
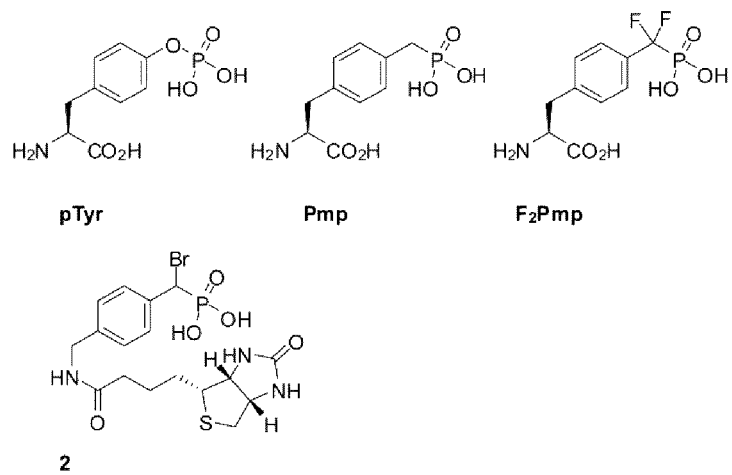
FIG. 1 is a general schematic diagram of reversible and irreversible PTP inhibitors of the prior art.
Figure 2:
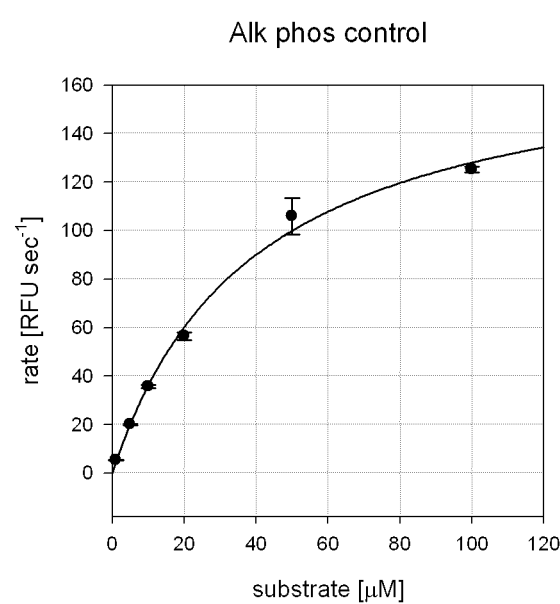
FIG. 2 is a plot of alkaline phosphatase enzyme activity in the presence of the fluorogenic substrate 6,8-difluoro-4-methylumbelliferyl phosphate ranging in concentration from 10 nM to 10 µM and in the absence of an inhibitor.
Figure 3:
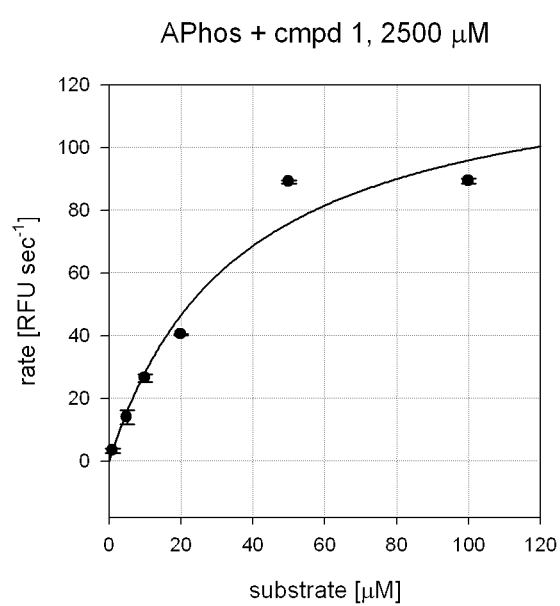
FIG. 3 is a plot of alkaline phosphatase enzyme activity in the presence of the fluorogenic substrate 6,8-difluoro-4-methylumbelliferyl phosphate ranging in concentration from 10 nM to 10 µM and in the presence of compound 1 at a concentration of 2500 µM.
Figure 4:
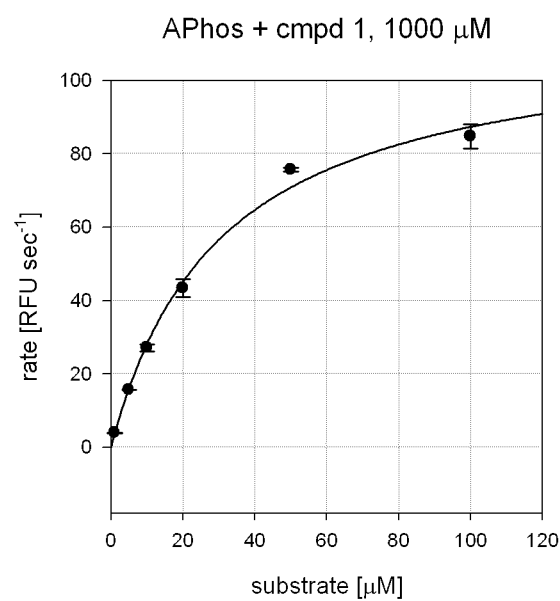
FIG. 4 is a plot of alkaline phosphatase enzyme activity in the presence of the fluorogenic substrate 6,8-difluoro-4-methylumbelliferyl phosphate ranging in concentration from 10 nM to 10 µM and in the presence of compound 1 at a concentration of 1000 µM.
Figure 5:
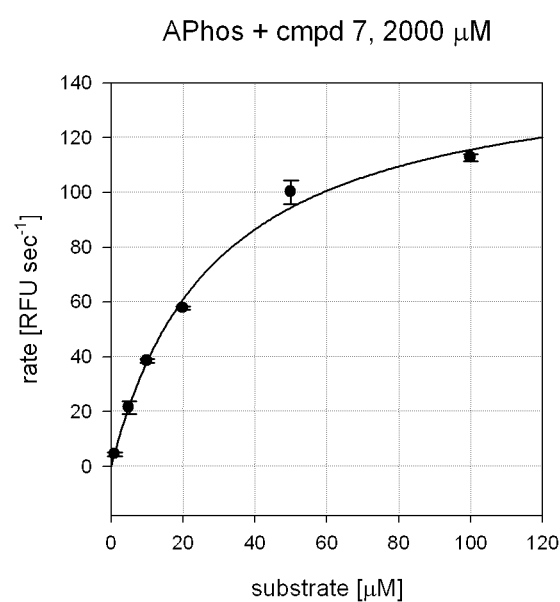
FIG. 5 is a plot of alkaline phosphatase enzyme activity in the presence of the fluorogenic substrate 6,8-difluoro-4-methylumbelliferyl phosphate ranging in concentration from 10 nM to 10 µM and in the presence of compound 7 at a concentration of 2000 µM.

The present invention relates to the preparation and use of novel bromo-phosphonomethylphenylalanine amino acid derivatives (BrPmp) and BrPmp-containing peptides as specific, irreversible protein tyrosine phosphatase inhibitors, which are suitable for application in peptide synthesis. The BrPmp derivatives of the present invention can be appropriately protected to allow for solid phase peptide synthesis (SPPS) and incorporation into peptides for preparation of protein tyrosine phosphatase inhibitors and inhibitor libraries. These derivatives are particularly advantageous since their synthesis is both easy and scalable, and they are suitable for peptide synthesis. This can allow for the synthesis of specific, irreversible PTP inhibitors, and overcome many of the disadvantages described above.

The present invention relates to BrPmp compounds of the Formula (I):

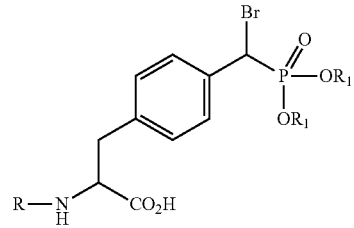

wherein R can be selected from the group consisting of Boc (butyloxycarbonyl), Fmoc (fluorenylmethyloxycarbonyl), Cbz (carboxybenzyl), Alloc (allyloxycarbonyl), and H (hydrogen); and wherein $R_1$ can be selected from the group consisting of methyl (—$CH_3$), ethyl (—$CH_2CH_3$), tert-butyl (—$C(CH_3)_3$), benzyl (—$CH_2C_6H_5$), allyl (—$CH_2CH=CH_2$), hydrogen (—H), dimethylamino (—$N(CH_3)_2$), propylamino (—$NHCH_2CH_2CH_3$), isopropylamino (—$NHCH(CH_3)_2$), and acetate (—$C(O)CH_3$).

The bromo-phosphonomethylphenylalanine amino acid derivatives of the Formula (I) can be L-amino acid derivatives or D-amino acid derivatives. The α-bromo substituent may be a mixture of diastereomers or a single R or S diastereomer.

Specific but not limiting examples of compounds of Formula (I) useful in the present invention include the following:

(1) compound of Formula I where R is hydrogen and $R_1$ is hydrogen;
(2) compound of Formula I where R is Fmoc and $R_1$ is methyl;
(3) compound of Formula I where R is Boc and $R_1$ is methyl;
(4) compound of Formula I where R is Cbz and $R_1$ is methyl;
(5) compound of Formula I where R is Fmoc and $R_1$ is ethyl;
(6) compound of Formula I where R is Boc and $R_1$ is ethyl;
(7) compound of Formula I where R is Cbz and $R_1$ is ethyl;
(8) compound of Formula I where R is Fmoc and $R_1$ is benzyl;
(9) compound of Formula I where R is Boc and $R_1$ is benzyl;
(10) compound of Formula I where R is Cbz and $R_1$ is benzyl;

(11) compound of Formula I where R is Fmoc and $R_1$ is dimethylamino (—N(CH$_3$)$_2$);
(12) compound of Formula I where R is Boc and $R_1$ is dimethylamino (—N(CH$_3$)$_2$);
(13) compound of Formula I where R is Cbz and $R_1$ is dimethylamino (—N(CH$_3$)$_2$);
(14) compound of Formula I where R is Fmoc and $R_1$ is propylamino (—NHCH$_2$CH$_2$CH$_3$);
(15) compound of Formula I where R is Boc and $R_1$ is propylamino (—NHCH$_2$CH$_2$CH$_3$);
(16) compound of Formula I where R is Cbz and $R_1$ is propylamino (—NHCH$_2$CH$_2$CH$_3$);
(17) compound of Formula I where R is Fmoc and $R_1$ is isopropylamino (—NHCH(CH$_3$)$_2$);
(18) compound of Formula I where R is Boc and $R_1$ is isopropylamino (—NHCH(CH$_3$)$_2$);
(19) compound of Formula I where R is Cbz and $R_1$ is isopropylamino (—NHCH(CH$_3$)$_2$);
(20) compound of Formula I where R is Fmoc and $R_1$ is allyl;
(21) compound of Formula I where R is Boc and $R_1$ is allyl; and
(22) compound of Formula I where R is Cbz and $R_1$ is allyl.

As one of skill in the art will appreciate, by selecting appropriate R and $R_1$ substituents, compounds of Formula I can be prepared to allow for application to peptide synthesis. Various techniques of peptide synthesis can be used, which can include, but are not limited to, solid-phase peptide synthesis (SPPS).

The present invention further relates to peptides of the Formula (II):

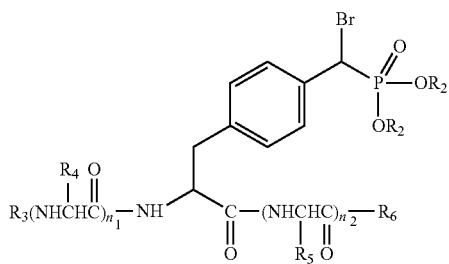

wherein $R_2$ can be selected from the group consisting of methyl (—CH$_3$), ethyl (—CH$_2$CH$_3$), tert-butyl (—C(CH$_3$)$_3$), benzyl (—CH$_2$C$_6$H$_5$), allyl (—CH$_2$CH═CH$_2$), hydrogen (—H), dimethylamino (—N(CH$_3$)$_2$), propylamino (—NHCH$_2$CH$_2$CH$_3$), isopropylamino (—NHCH(CH$_3$)$_2$), and acetate (—C(O)CH$_3$);
wherein $R_3$ can be selected from the group consisting of hydrogen, acetyl, alkanoyl, alkyl, aryl, aralkyl, alkaryl, H (hydrogen), and polyethyleneoxy;
wherein $R_4$ and $R_5$ are side chains of amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine, or derivatives thereof;
wherein $R_6$ can be selected from the group consisting of hydroxyl, —NH$_2$, O-alkyl, O-aryl, O-aralkyl, O-alkaryl, and N-polyethyleneoxy; and
wherein $n_1$ and $n_2$ may be the same or different, are zero, or 1-50, but wherein $n_1$ and $n_2$ are not zero at the same time, with the proviso that the substituents of Formula II which can be substituted are optionally substituted.

Alkyls occurring in Formula II can be alkyls which are $C_{1-20}$ alkyl. Aryls occurring in Formula II can be aryls which are $C_{6-10}$ aryl.

When substituted alkyls occur in Formula II, examples of suitable substituents are hydroxyl, halogen, alkoxy, haloalkoxy, and alkoxyalkyl; and wherein the alkyl groups and the alkyl groups of the alkaryl and aralkyl groups herein are linear or branched chain, or cyclic having up to 10 carbon atoms.

When substituted heteroaryl groups occur in Formula II, examples of suitable substituents are halogen, nitro, cyano, or haloalkyl groups; and wherein the alkyl, haloalkyl, alkenyl, haloalkenyl, alkoxy, and haloalkoxy groups herein are linear or branched chains, having less than 10 carbon atoms, and the halo substitution in all these groups consists of one or more halogen atoms, which are the same or different, from mono substitution up to complete poly substitution.

The amino acids and amino acid derivatives of the Formula (II) can be L-amino acids, L-amino acid derivatives, D-amino acids, or D-amino acid derivatives. The α-bromo substituent may be a mixture of diastereomers or a single R or S diastereomer.

As one of skill in the art will appreciate, compounds of Formula II may consist of any number of amino acids. The amino acid sequence of the peptide depends upon the particular use of the peptide. For example, the design of a peptide for use as a PTP inhibitor will be directed toward the amino acid sequence of the particular PTP, which may vary greatly between PTPs. As will be understood by one of skill in the art, the final peptide sequence will be selected so as to impart the highest level of specificity towards a specific PTP.

In one embodiment of the present invention, the substituents of compounds of Formula II can be further substituted with a reporter group. The reporter group may be selected from the group consisting of fluorescent tags, chemiluminescent tags, a solid support, reactive groups (which can include, but are not limited to, azide, alkyne, amino-oxy, or hydrazine), and an affinity tag.

In one embodiment of the present invention, the peptide of Formula II is a tripeptide, wherein $R_3$ is hydrogen, $R_4$ is the side chain of aspartic acid, $n_1$ is 1, $R_2$ is hydrogen, $R_5$ is the side chain of leucine, $R_6$ is hydroxyl, and $n_2$ is 1.

The BrPmp amino acid derivatives and BrPmp-containing peptides of the present invention may exist in a free form (i.e., unprotected) or in a protected form. The protected form refers to compounds wherein one or more reactive groups (i.e. N-terminal amino groups or —OH groups) are covered by a protecting group. Of course, one of skill in the art will appreciate that many different protecting groups can be used within the scope of the present invention.

The peptides of the present invention, whether they are in free or protected form, may exist as salts or as complexes. Acid addition salts may be formed with organic acids, polymeric acids, and inorganic acids, for example, which are not meant to be limiting. Such acid addition salt forms include, but are not limited to, the hydrochlorides and acetates. Complexes are defined as compounds of known type, formed on addition of inorganic substances, such as inorganic salts and/or on addition of polymeric organic substances.

The present invention further provides for the use of compounds of Formula I and Formula II to inhibit PTPs. The compounds of the present invention can be used to inhibit PTPs in cell-free extracts as well as in whole cells.

In one embodiment of the invention, a library of compounds of Formula II may be synthesized to screen for high potency, irreversible PTP inhibitors and identify new PTP-specific substrate sequences.

In one embodiment of the invention, a library of compounds of Formula II may be incorporated into a multiplexed detection kit. The detection kit may include many different BrPmp-containing peptide sequences that can be used to profile PTP activity in cell lysate or diagnostic samples, such as human or animal sera or biopsy samples.

The following MATERIALS AND METHODS were used in the examples that follow. These materials and methods are for illustrative purposes only and are not to be construed as limiting the scope of the invention in any way. One of skill in the art will appreciate that several modifications and substitutions can be made without affecting the scope of the invention. More specifically, these include modifications and substitutions in the specific techniques and reaction conditions listed below.

General Methods

Dry solvents (CH$_2$Cl$_2$, MeOH, CH$_3$CN, DMF) were purchased from Sigma Aldrich in capped DriSolv®; bottles, used without purification and were stored under argon. Toluene and pyridine were dried on molecular sieves and stored under desiccated atmosphere. D-Erythro-sphingosine and 1,2-dimyristoyl-sn-glycerol were purchased from Avanti polar lipids and stored under argon at −20° C. All other reagents used were purchased from commercial sources and were used without additional purification. All reactions were conducted under a stream of argon at ambient temperature and monitored by TLC on silica gel G-25 UV254 (0.25 mm). Developed TLC plates were visualized under UV lamp and charred by heating plates that were dipped in cerium molybdate stain or phosphomolybdic acid (PMA) stain. Flash column chromatography was performed using a chromatography system with flash silica gel columns (40-63 μm). The purification of polar lipids were performed by manual column chromatography with Iatrobeads (beaded silica gel 60 μm, 6RS-8060, Iatron Laboratories, Tokyo) using a CH$_2$Cl$_2$:MeOH:H$_2$O solvent mixture. NMR experiments were conducted using 400, 500, or 600 MHz instruments. Chemical shifts are relative to the deuterated solvent peak1 and are in parts per million (ppm). $^1$H NMR and $^{13}$C peak assignments were made on the basis of 2D-NMR such as COSY and HSQC experiments. Optical rotations were measured at 21±2° C. at the sodium D line (589 nm). ESI-MS spectra were carried out on samples suspended in solvent with added NaCl. Circular dichroism data was taken at 20° C.

In order that the invention be more fully understood, the following examples are set forth. These examples are for illustrative purposes only and are not to be construed as limiting the scope of the invention in any way. Moreover, these examples are not intended to exclude equivalents and variations of the present invention, which are apparent to one skilled in the art.

EXAMPLE 1

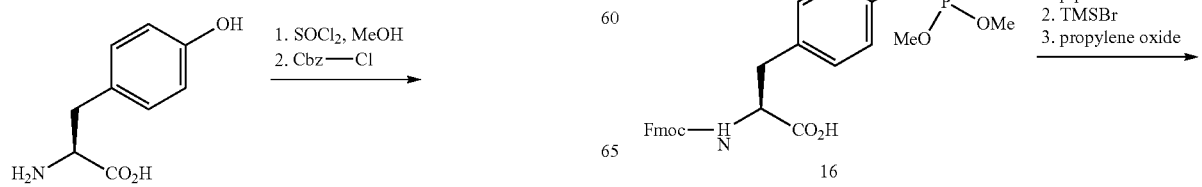

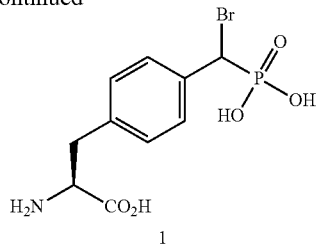

1

Synthesis of methyl 2-{[(benzyloxy)carbonyl]amino}-3-(4-hydroxyphenyl)propanoate (10)

Thionyl chloride (4.6 mL, 63.33 mmol, 2 eq) was added dropwise to dry MeOH (65 mL) at 0° C. and stirred for 5 min. Tyrosine (5.70 g, 31.5 mmol, 1 eq) was then added and the reaction vessel was fitted with a drying tube filled with drierite and slowly allowed to come to room temperature over 21 h. The solvent was then evaporated and crude product dried over high vacuum for 8 h. The crude product was then dissolved in a 1:1 mixture of acetone (63 mL) and a 7% solution of $Na_2CO_3$ in water (63 mL). Benzyl chloroformate (4.7 mL, 34.7 mmol, 1.2 eq) was then added dropwise and the reaction was stirred for 3 h at room temperature. Ethyl acetate was then added (300 mL), and the organic layer was washed with water (100 mL), brine (100 mL) and dried over $Na_2SO_4$. The solvent was evaporated to give 10 as a viscous yellow oil (10.37 g). The product was used in the next step without purification.

Synthesis of methyl 2-{[(benzyloxy)carbonyl]amino}-3-(4-{[(trifluoromethyl)sulfonyl]oxy}phenyl)propanoate (11)

Compound 10 (10.37 g, 31.5 mmol, 1 eq) and N-phenyl bis-trifluoromethane sulfonamide (12.39 g, 34.65 mmol, 1.1 eq) were dissolved in acetonitrile (150 mL). $Et_3N$ (5.3 mL, 37.8 mmol, 1.2 eq) was then added and the reaction was stirred for 3 h. The reaction mixture was then diluted with ethyl acetate (150 mL) and water (100 mL). The organic layer was washed with brine, dried over $Na_2SO_4$ and the solvent was evaporated. The product was purified on a silica column (3:2 hexane:ethyl acetate followed by 2:3 hexanes:ethyl acetate) to obtain 14.38 g (99% yield) as a white solid. $^1$H NMR (400 MHz, $CDCl_3$) δ 7.37-7.32 (m, 5H), 7.21-7.14 (m, 4H), 5.28 (d, J=7.5 Hz, 1H), 5.11 (d, J=12.3 Hz, 1H), 5.07 (d, J=12.3 Hz, 1H), 4.66 (dd, J=6.3, 13.9 Hz, 1H), 3.71 (s, 3H), 3.19 (dd, J=5.8, 13.9 Hz, 1H), 3.08 (dd, J=6.3, 13.9 Hz, 1H); ESIMS calculated for $C_{19}H_{18}F_3NO_7S$ [M+Na]$^+$484.07, found: 484.08; mp 70-73° C.

Synthesis of methyl 2-{[(benzyloxy)carbonyl]amino}-3-[4-(hydroxymethyl)phenyl]propanoate (12)

Compound 11 (7.70 g, 16.70 mmol, 1 eq), $Pd(OAc)_2$ (378 mg, 1.68 mmol, 0.1 eq) and 1,1'-Bis(diphenylphosphino)ferrocene (dppf) (1.86 g, 3.34 mmol, 0.2 eq) were dissolved in dry DMF (40 mL). $K_2CO_3$ (11.54 g, 83.5 mmol, 5 eq) was then added to the reaction mixture and CO gas was bubbled through for 15 min. The reaction mixture was then heated at 60° C. for 8 h under a CO balloon. The reaction mixture was then cooled and partitioned between ethyl acetate and saturated $NHCO_3$. The aqueous layer was acidified with a 10% aqueous solution of citric acid and extracted with ethyl acetate (4×75 mL). The organic layer was washed with brine, dried over $Na_2SO_4$ and the solvent was evaporated to give the crude carboxylic acid as a tan-coloured solid (4.89 g). The acid was dried over $P_2O_5$ and was used in the next step without purification. The crude acid was dissolved in dry THF (70 mL) and cooled in an ice bath. The reaction was charged with $BH_3$-DMS complex (10 M, 6.96 mL, 68.47 mmol, 4 eq) added dropwise. The reaction mixture was warmed to room temperature over 2 h. A solution of saturated $NaHCO_3$ was added dropwise until the bubbling ceased. Ethyl acetate (70 mL) was added and the organic layer was separated and dried over $Na_2SO_4$ and then reduced. The crude product was purified on a silica column (3:2 hexane:ethyl acetate followed by 2:3 hexanes:ethyl acetate) to give 12 (3.56 g, 62%) as a white solid. $[α]_D^{25}$+50.56° (C=0.99, $CHCl_3$). $^1$H NMR (400 MHz, $CDCl_3$) δ 7.41-7.29 (m, 5H), 7.29-7.23 (m, 2H), 7.08 (d, J=8.0 Hz, 2H), 5.14-4.87 (m, 2H), 4.65 (dd, J=10.2, 5.8 Hz, 3H), 3.70 (d, J=18.6 Hz, 3H), 3.10 (qd, J=13.9, 5.8 Hz, 2H), 1.86 (t, J=5.8 Hz, 1H). $^{13}$C NMR (101 MHz, $CDCl_3$) δ 172.17 (s), 155.86 (s), 140.04 (s), 136.45 (s), 135.29 (s), 129.68 (s), 128.75 (s), 128.43 (s), 128.32 (s), 127.49 (s), 67.22 (s), 65.20 (s), 55.03 (s), 52.59 (s), 38.12 (s). ESIMS calculated for $C_{19}H_{21}NO_5Na$ [M+Na]$^+$366.13, found: 366.13; mp 74-77° C.

Synthesis of L-Phenylalanine, 4-[(dimethyloxyphosphinyl)hydroxymethyl]-N-[(phenylmethoxy)carbonyl]-, methyl ester (13)

Compound 12 (3.56 g, 10.37 g, 1 eq) was dissolved in DMSO (22 mL) and 2-iodoxybenzoic acid (3.77 g, 13.48 mmol, 1.3 eq) was added and the reaction mixture and stirred for 1 h. The reaction mixture was then diluted with water (60 mL) and ether (60 mL) and filtered. The organic layer was separated and washed with water (2×50 mL), brine and dried over $Na_2SO_4$. The solvent was evaporated and the crude aldehyde was used immediately in the next step without purification. The aldehyde was dissolved in dimethyl phosphite (1.05 mL, 11.41 mmol 1.1 eq) with mild heating. CsF (9.45 g, 62.22 mmol, 6 eq) was added and the reaction was stirred until it solidified. The crude product was then dissolved in DCM (40 mL), filtered, and the solvent evaporated. The crude product was purified on a silica plug (first with ether, then 1:20 DCM:MeOH) to give 13 as a white solid (3.98 g, 85%). $[α]_D^{25}$+38.08° (C=1.55, $CHCl_3$). NMR (400 MHz, $CDCl_3$) δ 7.40 (dd, J=8.1, 1.9 Hz, 2H), 7.37-7.27 (m, 5H) 7.11 (d, J=8.0 Hz, 2H), 5.39-5.26 (m, 1H), 5.07 (s, 2H), 5.00 (d, J=11.0 Hz, 1H), 4.63 (d, J=7.6 Hz, 1H), 3.69 (d, J=2.8 Hz, 3H), 3.65 (d, J=4.7 Hz, 3H), 3.62 (s, 3H), 3.09 (dd, J=16.1, 3.3 Hz, 2H).

$^{13}$C NMR (101 MHz, $CDCl_3$) δ 172.12 (s), 155.86 (s), 136.30 (d, $J_{C-P}$=23.9 Hz), 135.50 (s), 129.59 (d, $J_{C-P}$=2.1 Hz), 128.76 (s), 128.44 (s), 128.33 (s), 127.53 (d, $J_{C-P}$=5.8 Hz), 70.60 (d, $J_{C-P}$=159.4 Hz), 67.24 (s), 55.04 (s), 54.04 (dd, $J_{C-P}$=18.6, 7.1 Hz), 52.57 (s), 38.19 (s). $^{31}$P NMR (162 MHz, $CDCl_3$) δ 24.53 (s, 87P), 11.64 (s, 1P). ESIMS calculated for $C_{21}H_{26}NO_8P$ [M+Na]$^+$474.13, found: 474.13; mp 68-71° C.

Synthesis of L-Phenylalanine, 4-[(dimethyloxyphosphinyl)bromomethyl]-N-[(9H-fluoren-9-ylmethoxy)carbonyl]-, methyl ester (14)

Compound 13 (3 g, 6.65 mmol, 1 eq) was dissolved in dry MeOH and Pd/C (200 mg, 30 mg/mmol) was added. A three way stopcock (connected to a $H_2$ balloon and vacuum line) was fitted to the reaction vessel. The reaction mixture was then flushed with $H_2$ (3×) and stirred at room temperature for 6 h. The reaction mixture was filtered through a celite pad and the solvent evaporated. A mixture of the residue, Fmoc-succinimide (2.35 g, 6.98 mmol, 1.05 eq) and NaHCO$_3$ (2.34 g, 27.92 mmol, 4 eq) in acetonitrile and water (1:1, 130 mL) was stirred at room temperature overnight. The acetonitrile was evaporated under reduced pressure and the crude product was extracted with ethyl acetate. The organic layer was dried over Na$_2$SO$_4$, evaporated under reduced pressure and purified on a silica plug (ether, followed by 10:1 DCM:MeOH) to give 14 as a white solid (3.59 g, 90%). $^1$H NMR (400 MHz, CDCl$_3$) δ 7.81-7.71 (m, 2H), 7.64-7.48 (m, 2H), 7.48-7.35 (m, 4H), 7.34-7.28 (m, 2H), 7.19-7.03 (m, 2H), 5.33 (d, J=7.8 Hz, 1H), 5.02 (d, J=11.0 Hz, 1H), 4.70-4.60 (m, 1H), 4.45-4.29 (m, 2H), 4.20 (s, 1H), 3.70 (d, J=7.0 Hz, 4H), 3.66 (dd, J=3.9, 1.0 Hz, 3H), 3.64-3.62 (m, 1H), 3.20-3.00 (m, J=5.1 Hz, 2H). $^{13}$C NMR (101 MHz, cdcl$_3$) δ 172.09 (s), 155.80 (s), 144.01 (d, J$_{C-P}$=7.5 Hz), 141.55 (s), 136.24 (s), 135.73-134.25 (m), 129.65 (s), 127.98 (s), 127.53 (d, J$_{C-P}$=5.8 Hz), 127.31 (s), 125.30 (d, J$_{C-P}$=6.1 Hz), 120.24 (s), 70.64 (d, J$_{C-P}$=159.5 Hz), 67.23 (s), 55.01 (s), 54.04 (dd, J$_{C-P}$=16.7, 7.1 Hz), 52.62 (s), 47.40 (s), 38.24 (s). $^{31}$P NMR (162 MHz, CDCl$_3$) δ 24.51 (s). ESIMS calculated for C$_{28}$H$_{30}$NO$_8$P [M+Na]$^+$562.16, found: 562.16; mp 65-70° C.

Synthesis of Synthesis of L-Phenylalanine, 4-[(dimethyloxyphosphinyl)bromomethyl]-N-[(9H-fluoren-9-ylmethoxy)carbonyl]-, methyl ester (15)

In a round bottom flask 14 (2 g, 3.70 mmol, 1 eq) was dissolved in dry DCM (30 mL) and dry pyridine (0.38 mL, 4.63 mmol, 1.25 eq) was added. Thionyl bromide (0.36 mL, 4.63 mmol, 1.25 eq) was then added to the round bottom flask under an inert atmosphere. The round bottom flask was sealed with a septum, cooled in an ice bath and slowly allowed to come to room temperature overnight. The solvent was then evaporated and the crude product was dissolved in ethyl acetate. The organic layer was washed with 1 M HCl, saturated NaHCO$_3$, water, and brine, dried over Na$_2$SO$_4$ and filtered. The solvent was evaporated and the crude product was purified on a silica plug (ether, followed by 10:1 DCM:MeOH) to give 15 as a white solid (1.14 g, 78%). [α]$_D^{25}$+34.72° (C=1.02, CHCl$_3$). $^1$H NMR (400 MHz, CDCl$_3$) δ 7.77 (d, J=7.5 Hz, 2H), 7.57 (d, J=7.4 Hz, 2H), 7.49 (d, J=7.5 Hz, 2H), 7.41 (t, J=7.4 Hz, 2H), 7.32 (t, J=7.5 Hz, 2H), 7.17-6.98 (m, 2H), 5.32-5.23 (m, 1H), 4.86 (d, J=13.1 Hz, 1H), 4.66 (dd, J=13.4, 6.1 Hz, 1H), 4.49-4.30 (m, 2H), 4.20 (t, J=6.9 Hz, 1H), 3.85 (d, J=10.8 Hz, 3H), 3.72 (s, 3H), 3.59 (dd, J=10.7, 3.8 Hz, 3H), 3.11 (qd, J=13.9, 5.9 Hz, 2H). $^{13}$C NMR (101 MHz, cdcl$_3$) δ 171.90 (s), 155.73 (s), 143.99 (d, J$_{C-P}$=6.5 Hz), 141.57 (s), 137.32 (s), 133.45 (s), 129.98 (d, J$_{C-P}$=3.6 Hz), 129.89 (s), 127.99 (s), 127.32 (s), 125.26 (d, J$_{C-P}$=7.6 Hz), 120.25 (s), 67.19 (d, J$_{C-P}$=6.2 Hz), 54.89 (ddd, J$_{C-P}$=24.4, 7.0, 1.4 Hz), 54.89 (s), 52.65 (s), 47.41 (s), 40.78 (d, J$_{C-P}$=160.0 Hz), 38.20 (d, J$_{C-P}$=7.0 Hz). $^{31}$P NMR (162 MHz, CDCl$_3$) δ 20.43 (s). ESIMS calculated for C$_{28}$H$_{29}$NO$_7$BrP [M+Na]$^+$ 624.08, found: 626.08; mp 68-71° C.

Synthesis of L-Phenylalanine, 4-[(dimethyloxyphosphinyl)bromomethyl]-N-[(9H-fluoren-9-ylmethoxy)carbonyl]; Fmoc-L-BrPmp(Me$_2$)—OH (16)

Compound 15 (3.00 g, 5.00 mmol, 1 eq) was dissolved in THF (35 mL) and cooled in an ice bath. LiOH (240 mg, 10.00 mmol, 2 eq) was dissolved in water (35 mL) and cooled in an ice bath. The lithium hydroxide solution was then added to the reaction mixture and stirred for 30 min. The THF was then evaporated, and the aqueous layer was washed with ether (30 mL). The aqueous layer was acidified to pH 2 with concentrated HCl and was extracted with ethyl acetate (4×75 ml). The combined organic layers were dried over Na$_2$SO$_4$, and concentrated to a white solid (2.67 g, 91% yield). [α]$_D^{25}$+40.24° (C=1.31, CHCl$_3$). $^1$H NMR (400 MHz, CDCl$_3$) δ 7.76 (d, J=7.2 Hz, 2H), 7.57 (d, J=6.3 Hz, 2H), 7.48-7.35 (m, 4H), 7.30 (t, J=7.2 Hz, 2H), 7.16 (s, 2H), 5.52 (d, J=13.1 Hz, 1H), 4.98-4.81 (m, 1H), 4.67 (s, 1H), 4.47 (d, J=7.3 Hz, 1H), 4.33 (s, 1H), 4.19 (s, 1H), 3.82 (d, J=10.7 Hz, 3H), 3.54 (t, J=10.4 Hz, 3H), 3.18 (s, 2H). $^{13}$C NMR (101 MHz, CDCl$_3$) δ 155.98 (s), 144.01 (d, J$_{C-P}$=10.5 Hz), 141.56 (s), 137.79 (s), 132.66 (s), 130.31 (s), 129.79 (d, J$_{C-P}$=5.5 Hz), 127.99 (s), 127.32 (s), 125.32 (d, J$_{C-P}$=7.5 Hz), 120.24 (s), 77.58 (s), 77.26 (s), 76.94 (s), 67.14 (s), 55.55-54.92 (m), 54.79 (s), 47.42 (s), 40.25 (dd, J$_{C-P}$=160.8, 7.6 Hz), 37.77 (s). $^{31}$P NMR (162 MHz, CDCl$_3$) δ 20.59 (d, J=38.6 Hz). ESIMS calculated for C$_{27}$H$_{27}$NO$_7$BrP [M+Na]$^+$610.06, found: 612.06; mp 84-88° C.

Synthesis of L-BrPmp-OH (1)

Compound 16 (200 mg, 0.34 mmol, 1 eq) was dissolved in a solution of 20% piperidine in dry DCM (10 mL) and stirred at room temperature for 30 min. The solvent was then evaporated and the residue was dried on high vacuum over P$_2$O$_5$ for 4 h. The residue was then dissolved in dry acetonitrile (10 mL) and TMSBr (0.47 mL, 3.4 mmol, 10 eq) was added under an inert atmosphere and the reaction mixture was stirred overnight. The organic solvent was evaporated and the crude residue was dissolved in anhydrous EtOH (3 mL), propylene oxide (36 µl, 0.51 mmol, 1.5 eq) was added and the reaction mixture was stirred overnight resulting in a white precipitate the next day. Water (5 mL) was added and the EtOH was then removed under reduced pressure. The aqueous layer was washed with ether (3 mL), filtered and freeze dried. The crude product was dissolved in water (1 mL) and passed through a C18 Sep-pak syringe column. The aqueous fractions were freeze dried yielding 1 (94 mg, 65%) as a white solid of the piperidine salt. [α]$_D^{25}$−16.56° (C=1.36, CHCl$_3$). $^1$H NMR (400 MHz, D$_2$O) δ 7.54 (d, J=7.8 Hz, 2H), 7.26 (d, J=7.6 Hz, 2H), 4.95 (d, J=11.6 Hz, 1H), 4.07-3.92 (m, 1H), 3.28 (d, J=10.5 Hz, 1H), 3.16-3.00 (m, 5H), 1.73 (dt, J=10.8, 5.5 Hz, 4H), 1.62 (dd, J=10.9, 5.7 Hz, 2H). $^{13}$C NMR (101 MHz, D$_2$O) δ 135.59 (s), 135.56 (d, J=1.1 Hz), 129.94 (d, J=5.8 Hz), 129.80 (d, J=1.4 Hz), 56.05 (s), 46.23 (s), 44.82 (s), 36.23 (s), 22.48 (s), 21.74 (s). $^{31}$P NMR (162 MHz, D$_2$O) δ 13.47 (s). ESIMS calculated for C$_{10}$H$_{12}$NO$_5$BrP [M-H]$^-$ 335.96, found: 335.96; decomp. 140° C.

EXAMPLE 2

Synthesis of Tripeptide Asp-BrPmp-Leu (17)

The tripeptide was assembled manually on Wang resin (0.6 mol/g) preloaded with an Fmoc protected Leu residue (Fmoc-L-Leu-OH). Following a standard protocol; Fmoc-L-BrPmp (Me$_2$)—OH 16 (2 eq) was coupled to the resin using HBTU (1.96 eq) in the presence of DIPEA (4 eq) in NMP for 3.5 h. The reaction was monitored by Kaiser test. The coupling was repeated using the same equivalents of Fmoc-L-BrPmp (Me$_2$)—OH, HBTU and DIPEA in NMP for 3.5 h. Fmoc-Asp (tBu)-OH (5 eq) was coupled using HBTU (4.9 eq) in the presence of DIPEA (10 eq) in NMP for 3.5 h. Fmoc deprotection was achieved with 20% piperidine in NMP. The resin was washed with NMP, AcOH, DCM, and MeOH. Immediately after washing the resin with AcCN, DCM and MeOH, a mixture of TFA/H$_2$O/TIPS (95:2.5:2.5) was added and the resin was shaken at room temperature for 3 h. The cleaved peptide was precipitated in ether, filtered, dissolved in a mixture of H₂O and AcCN and lyophilized. The lyophilized peptide was suspended in AcCN, and TMSI (20 eq) was added under an inert atmosphere and the reaction mixture shaken for 100 min at room temperature. The AcCN/TMSI solution was evaporated under reduced pressure, and the crude product was dissolved in water and washed with ether (3×) and the aqueous layer was lyophilized. The peptide was purified by HPLC (C-18 semipreparative column) using a linear gradient (AcCN/H₂O mobile phase containing 0.1% TFA). 4 mg of pure compound was recovered from 18 mg crude product (33% of theoretical yield). $^1$H NMR (500 MHz, D₂O) δ 7.57 (d, J=6.8 Hz, 2H), 7.30 (dd, J=7.9, 2.2 Hz, 2H), 5.02 (d, J=11.7 Hz, 1H), 4.73 (dd, J=14.4, 7.1 Hz, 1H), 4.43-4.32 (m, 1H), 4.32-4.22 (m, 1H), 3.23-3.06 (m, 2H), 2.99-2.84 (m, 2H), 1.67-1.59 (m, 2H), 0.92 (dd, J=19.7, 4.7 Hz, 6H). $^{31}$P NMR (162 MHz, D₂O) δ 13.78 (d, J=4.8 Hz). ESIMS calculated for C₂₀H₂₉N₃O₉BrP [M-H]⁻ 564.08, found: 564.07.

EXAMPLE 3

Synthesis of dimethyl [hydroxy(phenyl)methyl]phosphonate (4)

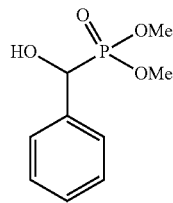 [SMILES: COP(=O)(OC)C(O)c1ccccc1]

Dimethyl phosphite (1.86 mL, 20.3 mmol, 1.03 eq) was added to benzaldehyde (2 mL, 19.8 mmol, 1 eq) and stirred for 5 min. KF (5.75 g, 99.0 mmol, 5 eq) was then added and the reaction mixture was stirred until it solidified (~20 min). The crude product was then dissolved in DCM, filtered, and the solvent evaporated yielding 4 as a white powder (4.38 g, 100%). The product was dried under high vacuum over P₂O₅. No further purification was required. $^1$H NMR (400 MHz CDCl₃) δ 7.53-7.45 (m, 2H), 7.43-7.23 (m, 3H), 5.05 (d, J=11.1 Hz, 1H), 3.67 (dd, J=14.3, 10.4 Hz, 6H). $^{13}$C NMR (101 MHz, CDCl₃) δ 136.66 (s), 128.64 (s), 128.49 (s), 127.28 (d, $J_{C-P}$=5.7 Hz), 70.86 (d, $J_{C-P}$=159.6 Hz), 54.02 (dd, $J_{C-P}$=28.4, 7.0 Hz). $^{31}$P NMR (162 MHz CDCl₃) δ 24.71 (s). ESIMS calculated for C₉H₁₃O₄PNa [M+Na]⁺ 239.06, found: 239.04; mp 85-86° C.

EXAMPLE 4

Synthesis of dimethyl [bromo(phenyl)methyl]phosphonate (5)

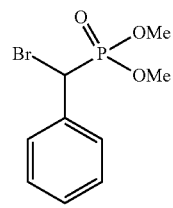

In a round bottom flask 4 (1 g, 4.63 mmol, 1 eq) was dissolved in dry DCM (10 mL) and dry pyridine (0.47 mL, 5.78 mmol, 1.25 eq) was added. Thionyl bromide (0.45 mL, 5.78 mmol, 1.25 eq) was then added to the round bottom flask under inert atmosphere. The round bottom flask was sealed with a septum, cooled in an ice bath and slowly allowed to come to room temperature overnight. The solvent was then evaporated and the crude product was dissolved in ethyl acetate. The organic layer was washed with 1 M HCl, saturated NaHCO₃, water, brine, then dried over Na₂SO₄ and filtered. The solvent was evaporated and the crude product was purified on a silica plug 1:4 (hexanes:ethyl acetate) followed by 3:7 (hexanes:ethyl acetate) to give 5 as a viscous oil (1.14 g, 88%). The product was dried under high vacuum over P₂O₅. $^1$H NMR (400 MHz, CDCl₃) δ 7.56 (d, J=7.8 Hz, 2H), 7.34 (d, J=7.5 Hz, 3H), 7.26 (s, 1H), 4.88 (d, J=13.1 Hz, 1H), 3.85 (d, J=10.8 Hz, 3H), 3.60 (d, J=10.7 Hz, 3H). $^{13}$C NMR (101 MHz, CDCl₃) δ 134.56 (d, $J_{C-P}$=3.3 Hz), 129.70 (d, $J_{C-P}$=6.7 Hz), 129.40 (d, $J_{C-P}$=2.2 Hz), 129.04 (d, $J_{C-P}$=1.3 Hz), 54.87 (dd, $J_{C-P}$=22.1, 7.0 Hz), 41.11 (d, $J_{C-P}$=159.9 Hz). $^{31}$P NMR (162 MHz, CDCl₃) δ 20.55 (s). ESIMS calculated for C₉H₁₂BrO₃PNa [M+Na]⁺300.96, found: 300.96.

EXAMPLE 5

Synthesis of [hydroxy(phenyl)methyl]phosphonic acid (6)

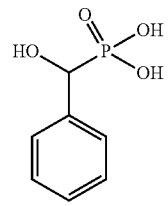

4 (0.15 g, 0.69 mmol, 1 eq) was dissolved in dry DCM (5 mL). TMSBr (0.77 mL, 5.52 mmol, 8 eq) was added to the solution under an inert atmosphere. The reaction was stirred for 20 h at room temperature. The solvent was then evaporated, and MeOH (5 mL) was added to the reaction mixture and stirred for 1 h. The solvent was evaporated and the crude product was dissolved in water (5 mL), filtered and freeze dried, yielding 6 as a white powder (130 mg, 70%). $^1$H NMR (400 MHz, D₂O) δ 7.52-7.31 (m, 5H), 4.99 (d, J=12.3 Hz, 1H). $^{13}$C NMR (101 MHz, D₂O) δ 137.45, 128.78 (d, $J_{C-P}$=2.3 Hz), 128.52 (d, $J_{C-P}$=2.9 Hz), 127.39 (d, $J_{C-P}$=5.7 Hz), 71.02 (d, $J_{C-P}$=158.3 Hz). $^{31}$P NMR (162 MHz D₂O) δ 20.98 (s). ESIMS calculated for C₇H₉O₄PNa [M+Na]⁺ 211.01, found: 211.02; mp 160-162° C.

EXAMPLE 6

Synthesis of [bromo(phenyl)methyl]phosphonic acid (7)

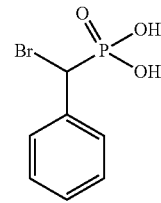

5 (0.3 g, 1.08 mmol, 1 eq) was dissolved in dry DCM (5 mL). TMSBr (1.2 mL, 8.64 mmol, 8 eq) was added under an inert atmosphere. The reaction was stirred for 20 h at room temperature. The solvent was then evaporated, and MeOH (5 mL) was added to the reaction mixture and stirred for 1 h. The solvent was evaporated and the crude product was dissolved in water (5 mL), filtered and freeze dried yielding 7 as a white powder (229 mg, 85%). $^1$H NMR (400 MHz, D$_2$O) δ 7.61-7.52 (m, 2H), 7.44-7.33 (m, 3H), 5.10-5.02 (m, 1H). $^{13}$C NMR (101 MHz, D$_2$O) δ 136.49 (d, $J_{C-P}$=3.3 Hz), 129.35 (d, $J_{C-P}$=6.0 Hz), 129.09 (s), 43.54 (s). $^{31}$P NMR (162 MHz, D$_2$O) δ 15.44 (s). ESIMS calculated for C$_7$H$_7$BrO$_3$P [M-H]$^-$ 248.93, found: 248.93 mp 158-60° C.

EXAMPLE 7

Phosphatase Enzyme Inhibition

Enzyme assays were conducted using human CD45-cytoplasmic domain (Enzo Life Science; diluted to 4 mU/μL in 50 mM HEPES, pH 7.2, 1 mM EDTA, and 0.1% nonidet P-40) (FIG. 6-8), or bovine alkaline phosphatase (New England Bio Labs; diluted to 4 mU/μL in 100 mM NaCl, 50 mM tris-HCl, 10 mM MgCl$_2$ 1 mM dithiothreitol, pH 7.9) (FIG. 2-5). Enzyme activity was detected with a fluorogenic substrate (6,8-difluoro-4-methylumbelliferyl phosphate; DiFMUP) (Invitrogen). Assays were performed in black 96-well plates and read in a Spectra Max M2 plate reader (Molecular Devices). For CD45 assays, substrate concentration was between 1 μM to 50 μM, for alkaline phosphatase substrate concentration was between 10 nM to 10 μM. Stock solutions of inhibitors (100 mM of compound 7 in deionized water; and 10 mM of compound 17 in 50% deionized water and 50% DMSO) were prepared and stored at −20° C. Final solutions in microplate wells contained a total volume of 100 μL consisting of 2 μL of diluted enzyme, inhibitor, and DiFMUP substrate diluted to 100 μL in the appropriate buffer. All wells were incubated for 10 min at 37° C. in the plate reader prior to the addition of DiFMUP. After incubation, substrate was added and the plate was read at an excitation maximum of 358 nm and an emission maximum of 450 nm every 30 seconds for 125 min (CD45) or 65 min (alkaline phosphatase).

Figure 6:
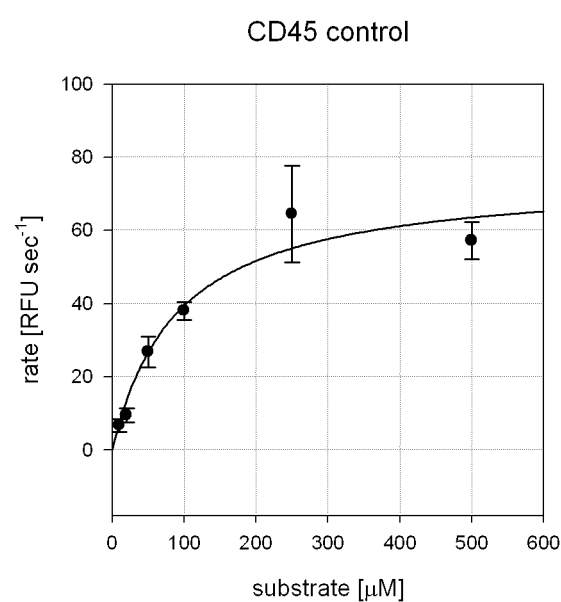
FIG. 6 is a plot of CD45 enzyme activity in the presence of the fluorogenic substrate 6,8-difluoro-4-methylumbelliferyl phosphate ranging in concentration from 1 µM to 50 µM and in the absence of an inhibitor.
Figure 7:
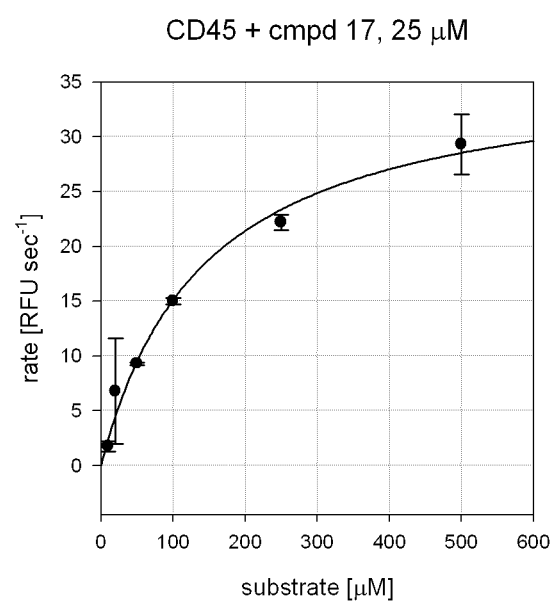
FIG. 7 is a plot of CD45 enzyme activity in the presence of the fluorogenic substrate 6,8-difluoro-4-methylumbelliferyl phosphate ranging in concentration from 1 µM to 50 µM and in the presence of compound 17 at a concentration of 25 µM.
Figure 8:
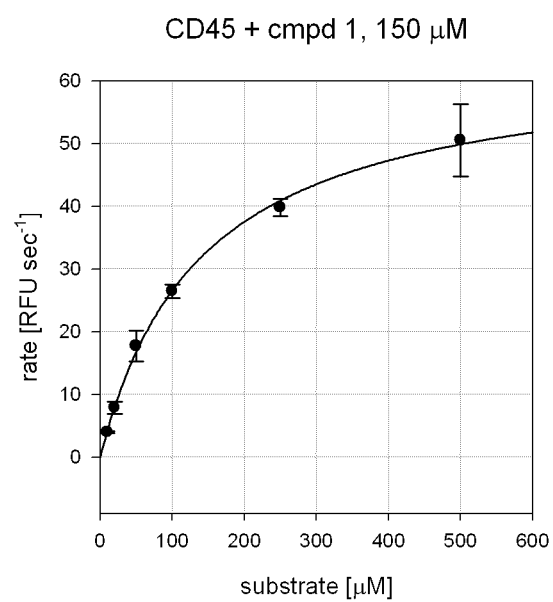
FIG. 8 is a plot of CD45 enzyme activity in the presence of the fluorogenic substrate 6,8-difluoro-4-methylumbelliferyl phosphate ranging in concentration from 1 µM to 50 µM and in the presence of compound 1 at a concentration of 150 µM.
Figure 9:
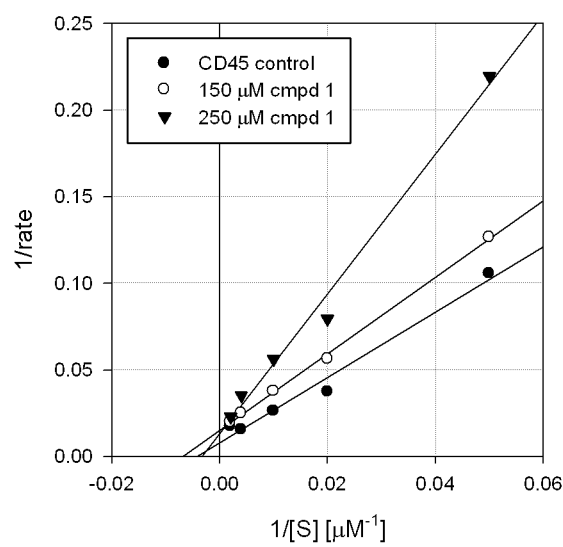
FIG. 9 is a Lineweaver-Burke reciprocal plot showing CD45 enzyme activity in the absence of inhibitor, in the presence of compound 1 at concentrations of 150 µM and 250 µM.
Figure 10:
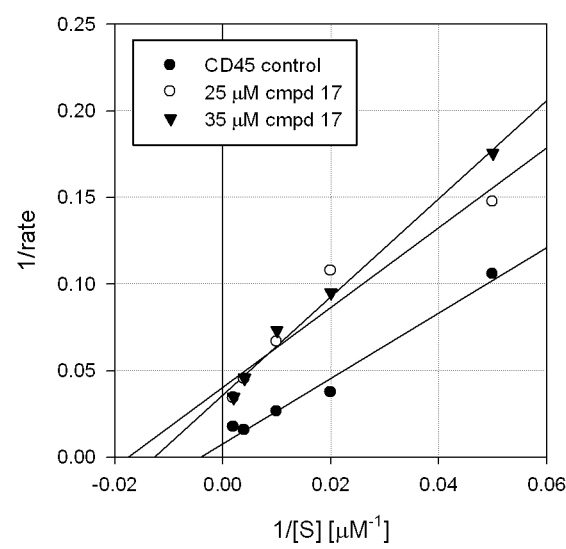
FIG. 10 is a Lineweaver-Burke reciprocal plot showing CD45 enzyme activity in the absence of inhibitor, in the presence of compound 17 at concentrations of 25 µM and 35 µM.
Figure 11:
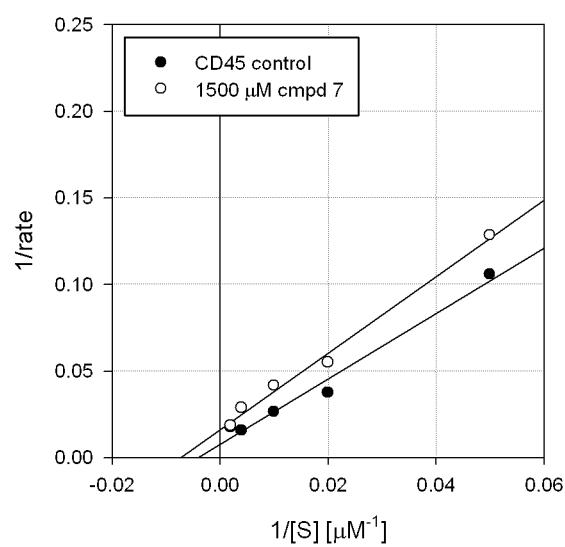
FIG. 11 is a Lineweaver-Burke reciprocal plot showing CD45 enzyme activity in the absence of inhibitor, in the presence of compound 7 at a concentration of 1500 µM.
Figure 12:
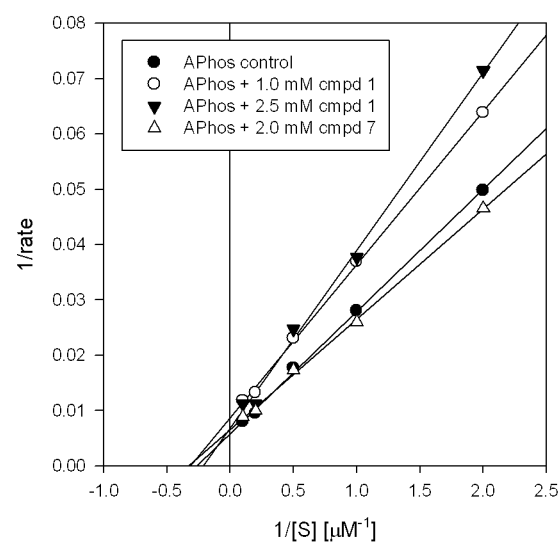
FIG. 12 is a Lineweaver-Burke reciprocal plot showing alkaline phosphatase enzyme activity in the absence of inhibitor, in the presence of compound 1 at concentrations of 1 mM and 2.5 mM, and the presence of compound 7 at a concentration of 2 mM.
Figure 13:
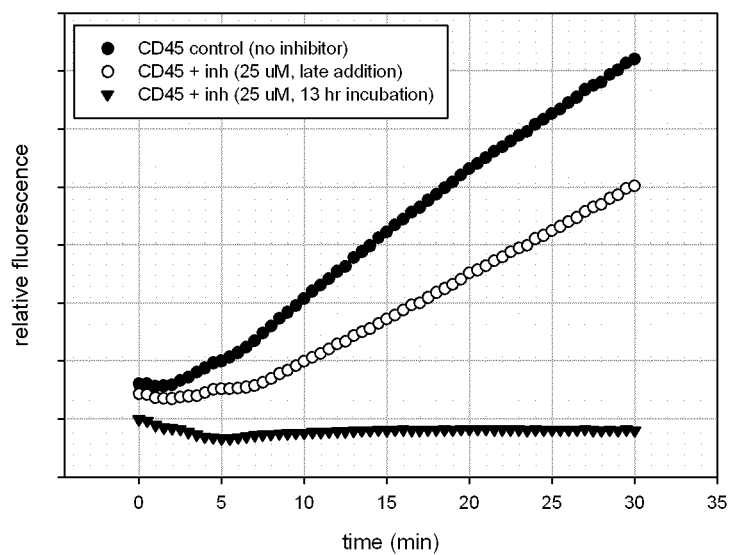
FIG. 13 is a plot of time-dependent inhibition of CD45 enzyme activity in the presence of compound 1 at a concentration of 25 µM. The enzyme was incubated for 13 h, either alone or in the presence of compound 1.

The $K_m$ for DiFMUP with each enzyme was first determined, and the experiment was then repeated in the presence of the inhibitor at a concentration close to an initially estimated K, (TABLE 1). For alkaline phosphatase, we found that none of the compounds tested showed significant inhibition of the enzyme (FIG. 2-5). However, in the case of the tyrosine phosphatase, CD45, we observed that both compound 1 and compound 17 showed significant inhibition of the enzyme at low micromolar concentrations (FIG. 6-8). The tripeptide was approximately 7-fold more potent than BrPmp alone, suggesting that the adjacent amino acid side chains contribute additional specificity. Previous reports of PTP inhibition using BBP analogs observed irreversible inhibition of the enzyme.(22) Evaluation of the kinetic data described above using reciprocal plots (FIG. 9-12) was not consistent with pure competitive inhibition of CD45, but this analysis is not conclusive on its own. Although these data are consistent with irreversible inhibition, a more conclusive experiment is presented in Example 8 below.

TABLE 1

Inhibition of alkaline phosphatase and CD45

| cmpd | enzyme | inhibitor [μM] | $K_{m, obs} \pm$ [μM]$^a$ | $K_I \pm$ [μM]$^b$ | $k_3 \pm$ [min$^{-1}$] |
|---|---|---|---|---|---|
| — | CD45 | 0 | 90 ± 20 | na | — |
| 1 | CD45 | 1500 | 99 ± 14 | na | — |
| 1 | CD45 | 150 | 141 ± 18 | 40 ± 8 | 0.041 ± 0.001 |
| 17 | CD45 | 35 | 141 ± 34 | 16 ± 4 | 0.048 ± 0.003 |

$^a$Values were determined by non-linear regression of the observed rate of reaction in the presence of inhibitor using the Michaelis-Menten equation. (24) Error is reported as the relative error from the fit.
$^b$For compounds 1 and 17, $K_I$ was determined by Kitz-Wilson analysis. The rate of enzyme inactivation, $k_3$, was also determined. (25)

EXAMPLE 8

Time-Dependent Inhibition of CD45 by Compound 1

To provide additional insight into the inhibition of these compounds, we obtained $K_I$ values using a Kitz-Wilson analysis.(24, 25) Compound 7 did not give a saturating curve in this analysis, and therefore could not be analyzed by this method, consistent with its failure to alter the rate of reaction (vide supra). Compound 7 has been previously tested as an inhibitor of the PTP Yop51, and exact kinetic constants were difficult to obtain, and we found similar difficulties for this determination with CD45.(21) Both compound 1 and 17 gave a saturating curve consistent with $K_I$ values of 40±8 μM and 16±4 μM, respectively. These results indicate that the tripeptide was approximately 4-fold more potent than BrPmp alone, suggesting that the adjacent amino acid side chains contribute additional specificity to the inhibitor. The Kitz-Wilson analysis estimated the rate of irreversible inhibition ($k_3$) of CD45 at 0.05 min$^{-1}$ for both compounds. To provide additional support for the expected mechanism of inhibition, we measured CD45 activity for an enzyme sample which was pre-incubated with the inhibitor and compared it to an enzyme sample that was only incubated with the inhibitor for a short period. We found that pre-incubation of the enzyme reduced activity, and at long incubation times completely inactivated the enzyme, confirming that the inhibitors act irreversibly at long incubation times.

REFERENCES

1. Petrone, A., and Sap, J. (2000) Emerging issues in receptor protein tyrosine phosphatase function: Lifting fog or simply shifting?, *J. Cell Sci.* 113, 2345-2354.
2. Moorhead, G. B. G., De Wever, V., Templeton, G., and Kerk, D. (2009) Evolution of protein phosphatases in plants and animals, *Biochem. J.* 417, 401-409.
3. Chan, A. C., Desai, D. M., and Weiss, A. (1994) The role of protein tyrosine kinase and protein tyrosine phosphatases in T cell antigen receptor signal transduction, *Annu. Rev. Immunol.* 12, 555-592.
4. Burke Jr, T. R., and Zhang, Z. Y. (1998) Protein-tyrosine phosphatases: Structure, mechanism, and inhibitor discovery, *Biopolymers* 47, 225-241.
5. Zhang, Z. Y. (2001) Protein tyrosine phosphatases: Prospects for therapeutics, *Curr. Opin. Chem. Biol.* 5, 416-423.
6. Hermiston, M. L., Xu, Z., and Weiss, A. (2003) CD45: A critical regulator of signaling thresholds in immune cells, in *Annu. Rev. Immunol.*, pp 107-137.
7. Hegedus, Z., Chitu, V., Toth, G. K., Finta, C., Varadi, G., Ando, I., and Monostori, E. (1999) Contribution of kinases and the CD45 phosphatase to the generation of tyrosine phosphorylation patterns in the T-cell receptor complex zeta chain, *Immunol. Lett.* 67, 31-39.
8. Wavreille, A. S., Garaud, M., Zhang, Y., and Pei, D. (2007) Defining SH2 domain and PTP specificity by screening combinatorial peptide libraries, *Methods* 42, 207-219.
9. Hubbard, C. E., and Barrios, A. M. (2008) A highly efficient route to enantiomerically pure 1-N-Bz-Pmp(t-Bu)2-OH and incorporation into a peptide-based protein tyrosine phosphatase inhibitor, *Bioorg. Med. Chem. Lett.* 18, 679-681.
10. Burke Jr, T. R., Smyth, M. S., Nomizu, M., Otaka, A., and Roller, P. P. (1993) Preparation of fluoro- and hydroxy-4-(phosphonomethyl)-D,L-phenylalanine suitably protected for solid-phase synthesis of peptides containing hydrolytically stable analogues of O-phosphotyrosine, *J. Org. Chem.* 58, 1336-1340.
11. Leung, C., Grzyb, J., Lee, J., Meyer, N., Hum, G., Jia, C., Liu, S., and Taylor, S. D. (2002) The difluoromethylenesulfonic acid group as a monoanionic phosphate surrogate for obtaining PTP1B inhibitors, *Bioorg. Med. Chem.* 10, 2309-2323.
12. Li, P., Zhang, M., Peach, M. L., Liu, H., Yang, D., and Roller, P. P. (2003) Concise and enantioselective synthesis of Fmoc-Pmp(But) 2-OH and design of potent Pmp-containing Grb2-SH2 domain antagonists, *Org. Lett.* 5, 3095-3098.
13. Qabar, M. N., Urban, J., and Kahn, M. (1997) A facile solution and solid phase synthesis of phosphotyrosine mimetic L-4-[diethylphosphono(difluoromethyl)]-phenylalanine (F2Pmp(EtO)2) derivatives, *Tetrahedron* 53, 11171-11178.
14. Yokomatsu, T., Yamagishi, T., Matsumoto, K., and Shibuya, S. (1996) Stereocontrolled synthesis of hydroxymethylene phosphonate analogues of phosphorylated tyrosine and their conversion to monofluoromethylene phosphonate analogues, *Tetrahedron* 52, 11725-11738.
15. Lee, K., Gao, Y., Yao, Z. J., Phan, J., Wu, L., Liang, J., Waugh, D. S., Zhang, Z. Y., and Burke Jr, T. R. (2003) Tripeptide inhibitors of Yersinia protein-tyrosine phosphatase, *Bioorg. Med. Chem. Lett.* 13, 2577-2581.
16. Saghatelian, A., and Cravatt, B. F. (2005) Assignment of protein function in the postgenomic era, *Nat. Chem. Biol.* 1, 130-142.
17. Sadaghiani, A. M., Verhelst, S. H. L., and Bogyo, M. (2007) Tagging and detection strategies for activity-based proteomics, *Curr. Opin. Chem. Biol.* 11, 20-28.
18. Lo, L. C., Pang, T. L., Kuo, C. H., Chiang, Y. L., Wang, H. Y., and Lin, J. J. (2002) Design and synthesis of classselective activity probes for protein tyrosine phosphatases, *J. Proteome Res.* 1, 35-40.
19. Liu, S., Zhou, B., Yang, H., He, Y., Jiang, Z. X., Kumar, S., Wu, L., and Zhang, Z. Y. (2008) Aryl vinyl sulfonates and sulfones as active site-directed and mechanism-based probes for protein tyrosine phosphatases, *J. Am. Chem. Soc.* 130, 8251-8260.
20. Park, J., and Pei, D. (2004) trans-β²-nitrostyrene derivatives as slow-binding inhibitors of protein tyrosine phosphatases, *Biochemistry* 43, 15014-15021.
21. Taylor, W. P., Zhang, Z. Y., and Widlanski, T. S. (1996) Quiescent affinity inactivators of protein tyrosine phosphatases, *Bioorg. Med. Chem.* 4, 1515-1520.
22. Kumar, S., Zhou, B., Liang, F., Wang, W. Q., Huang, Z., and Zhang, Z. Y. (2004) Activity-based probes for protein tyrosine phosphatases, *Proc. Natl. Acad. Sci. U.S.A.* 101, 7943-7948.
23. Mitra, S., and Barrios, A. M. (2008) Identifying selective protein tyrosine phosphatase substrates and inhibitors from a fluorogenic, combinatorial peptide library, *ChemBioChem* 9, 1216-1219.
24. Copeland, R. A. (2000) *Enzymes: a practical introduction to structure, mechanism, and data analysis,* 2nd ed., John Wiley & Sons, Inc., New York, N.Y.
25. Kitz, R., and Wilson, I. B. (1962) Esters of methanesulfonic acid as irreversible inhibitors of acetylcholinesterase, *J. Biol. Chem.* 237, 3245-&.

What is claimed is:
1. A compound of Formula (I) or Formula (II):

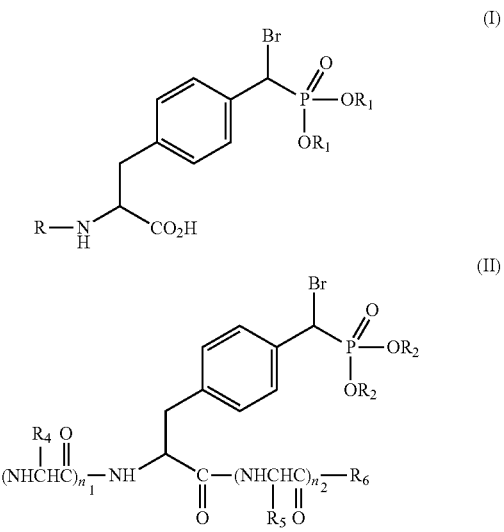

or a salt thereof;
wherein R is Boc (butyloxycarbonyl), Fmoc (fluorenylmethyloxycarbonyl), Cbz (carboxybenzyl), or Alloc (allyloxycarbonyl);
each $R_1$ is independently methyl (—$CH_3$), ethyl (—$CH_2CH_3$), tert-butyl (—$C(CH_3)_3$), benzyl (—$CH_2C_6H_5$), allyl (—$CH_2CH=CH_2$), dimethylamino (—$N(CH_3)_2$), propylamino (—$NHCH_2CH_2CH_3$), isopropylamino (—$NHCH(CH_3)_2$), or acetate (—$C(O)CH_3$);
each $R_2$ is independently methyl (—$CH_3$), ethyl (—$CH_2CH_3$), tert-butyl (—$C(CH_3)_3$), benzyl (—$CH_2C_6H_5$), allyl (—$CH_2CH=CH_2$), hydrogen (—H), dimethylamino (—$N(CH_3)_2$), propylamino (—$NHCH_2CH_2CH_3$), isopropylamino (—$NHCH(CH_3)_2$), or acetate (—$C(O)CH_3$);
$R_3$ is hydrogen, acetyl, alkanoyl, alkyl, aryl, aralkyl, alkaryl, or polyethyleneoxy;
$R_4$ and $R_5$ are side chains of amino acids selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine;
$R_6$ is hydroxyl, $NH_2$, O-alkyl, O-aryl, O-aralkyl, O-alkaryl, and N-polyethyleneoxy; and
each of $n_1$ and $n_2$ is independently zero or 1-50, wherein $n_1$ and $n_2$ are not zero at the same time, wherein alkyl groups of the compound of Formula (II) are optionally substituted with one or more substituents selected from the group consisting of hydroxyl, halogen, alkoxy, haloalkoxy and alkoxyalkyl; and wherein the compound of Formula II is optionally substituted with a group selected from a fluorescent tag, a chemiluminescent tag, an affinity tag, an azide, an alkyne, an amino-oxy, or a hydrazine.

2. The compound of Formula (I) of claim 1, wherein R is Fmoc and each $R_1$ is methyl.

3. The compound of Formula (I) of claim 1, wherein R is Fmoc, Boc, or Cbz and $R_1$ is methyl, ethyl, benzyl, dimethylamino (—N(CH$_3$)$_2$), propylamino (—NHCH$_2$CH$_2$CH$_3$), isopropylamino (—NHCH(CH$_3$)$_2$) or allyl.

4. The compound of Formula (I) of claim 1, which is an L-amino acid derivative.

5. The compound of Formula (I) of claim 1, which is a D-amino acid derivative.

6. The compound of Formula (II) of claim 1, wherein $R_3$ is hydrogen, $R_4$ is the side chain of aspartic acid, $n_1$ is 1, each $R_2$ is hydrogen, $R_5$ is the side chain of leucine, $R_6$ is hydroxyl, and $n_2$ is 1.

7. The compound of Formula (II) of claim 1, wherein the amino acids are selected from the group consisting of L-amino acids, L-amino acid derivatives, D-amino acids, and D-amino acid derivatives.

8. The compound of claim 2, which is an L-amino acid derivative.

9. The compound of claim 1, wherein R is Fmoc, Boc, or Cbz.

\* \* \* \* \*